United States Patent [19]

Stirling et al.

[11] Patent Number: 5,300,437
[45] Date of Patent: Apr. 5, 1994

[54] ENANTIOMERIC ENRICHMENT AND STEREOSELECTIVE SYNTHESIS OF CHIRAL AMINES

[75] Inventors: David I. Stirling, Branchburg; George W. Matcham, Bridgewater; Andrew L. Zeitlin, Millington, all of N.J.

[73] Assignee: Celgene Corporation, Warren, N.J.

[21] Appl. No.: 959,147

[22] Filed: Oct. 9, 1992

Related U.S. Application Data

[63] Continuation-in-part of Ser. No. 549,830, Jul. 9, 1990, Pat. No. 5,169,780, which is a continuation-in-part of Ser. No. 430,433, Nov. 1, 1989, abandoned, and Ser. No. 369,723, Jun. 22, 1989, Pat. No. 4,950,606.

[51] Int. Cl.$^5$ .............. C12P 13/02; C12P 7/26; C12P 7/38
[52] U.S. Cl. .................. 435/280; 435/129; 435/148; 435/149
[58] Field of Search ............. 435/280, 129, 148, 149

[56] References Cited

U.S. PATENT DOCUMENTS 4,806,473  2/1989  Johansen et al. .............. 435/71

FOREIGN PATENT DOCUMENTS

| | | |
|---|---|---|
| 222561 | 5/1987 | European Pat. Off. |
| 239122 | 9/1987 | European Pat. Off. |
| 2174964 | 3/1973 | France |
| 55-138389 | 10/1980 | Japan |
| 59-39294 | 3/1984 | Japan |
| 63-237796 | 10/1988 | Japan |
| 58-198296 | 11/1988 | Japan |
| 63-273486 | 11/1988 | Japan |

OTHER PUBLICATIONS

Chen, Y, et al., BBRC 77:688-92 (1977).
Lucher, L., et al., Antimicrob Agents and Chemo. 33:452-459 (1989).
Waters et al. FEMS Micro. Lett. 34 (1986) 279-282.
Cooper et al., Arch. Biochem. Biophys., 239, 556-566 (1985).
Chia et al., Life Sciences, 34, 2443-2452.
"Enzyme Nomenclature", Academic Press, Inc. (1984) pp. 220-231.
"Vitamin $B_6$ Pyridoxal Phosphate", D. Dolphin et al., Ed., John Wiley & Sons, pp. 117 and 118.
Nakano et al., J. Biochem., 82, 1375-1381 (1977).
Burnett et al., J. C. S. Chem. Comm., 1979, 826-828.
Tanizawa et al., Biochem. 21, 1104-1108 (1982).
Yonaha et al., Agric. Biol. Chem., 41 (9), 1701-1706 (1977).
Yonaha et al., Agric. Biol. Chem., 42 (12), 2362-2367 (1978).
Yonaha et al., Agric. Biol. Chem., 47 (10), 2257-2265 (1983).

Primary Examiner—Douglas W. Robinson
Assistant Examiner—S. Saucier
Attorney, Agent, or Firm—Mathews, Woodbridge & Collins

[57] ABSTRACT

Amines in which the amino group is on a secondary carbon atom which is chirally substituted can be enantiomerically enriched by the action of an omega-amino acid transaminase which has the property of preferentially converting one of the two chiral forms to a ketone. The process also can be used to stereoselectively synthesize one chiral form from ketones substantially to the exclusion of the other.

16 Claims, No Drawings

ENANTIOMERIC ENRICHMENT AND STEREOSELECTIVE SYNTHESIS OF CHIRAL AMINES

CROSS-REFERENCE TO RELATED APPLICATIONS

This is a continuation-in-part of Ser. No. 07/549,830 filed Jul. 9, 1990, now U.S. Pat. No. 5,169,780, which in turn is a continuation-in-part of Ser. No. 369,723 filed Jun. 22, 1989, now U.S. Pat. No. 4,950,606, and Ser. No. 430,433 filed Nov. 1, 1989, now abandoned, the disclosures of which are incorporated herein by reference.

The present invention relates to the enantiomeric enrichment and stereoselective synthesis of chiral amines.

BACKGROUND OF THE INVENTION

The biological activity of chemical products such as pharmaceuticals and agricultural products which possess a center of chirality often is found to reside principally in one of the possible chiral forms. Since most chemical syntheses are not inherently stereoselective, this poses a serious chemical processing problem. Enrichment in favor of one chiral form thus will be required at some stage, either the final chiral compounds or chemical precursors which possess the same center of chirality. Whatever stage is selected for the enrichment, and in the absence of a method of recycling of the unwanted enantiomer, the process is inherently limited to a maximum theoretical yield of 50% for the desired enantiomer.

Many of the chiral compounds of this type are amines. Moreover because of their synthetic versatility, amines also are good candidates for resolution, after which stereoselective conversion to the chiral compound can be effected. Chemical production of a chiral amine free of its enantiomer heretofore has relied on largely on resolution of a mixture of the two chiral forms through formation of diastereomeric derivatives such as a salt with a chiral acid, stereoselective syntheses, or the use of chiral chromatographic columns. See for examples U.S. Pat. No. 3,944,608 and EPA 36,265.

Some structural types of amines lend themselves to enzymatic resolution. Enzymatic reactions involving α-amino acids are well known and their use has been proposed for stereospecific preparations. U.S. Pat. No. 3,871,958, for example, discloses the enzymatic preparation of derivatives of the α-amino acid serine by coupling an aldehyde with glycine in the presence of a threoninealdolase, derived from an *E. coli* species, as well as a related synthesis of serinol employing ethanolamine.

Relatively little has been reported on enzymatic reactions on amino acids in which the amino group is not vicinal to a carboxylic acid group. Yonaha et al., *Agric. Biol. Chem.*, 42 (12), 2363-2367 (1978) describe an omega-amino acid:pyruvate transaminase found in a Pseudomonas species for which pyruvate was the exclusive amino acceptor. This enzyme, which had been previously crystallized and characterized see {Yonaha et al., *Agric. Biol. Chem.*, 41 (9), 1701-1706 (1977)} had low substrate specificity for omega amino acids such as hypotaurine, 3-aminopropane sulfonate, β-alanine, 4-aminobutyrate, and 8-aminooctanoate and catalyzed transaminations between primary aminoalkanes and pyruvate.

Nakano et al., *J. Biochem.*, 81, 1375-1381 (1977) identified two omega-amino acid transaminases in *B. cereus*: a β-alanine transaminase, which corresponds to Yonaha et al.'s omega-amino acid:pyruvate transaminase, and a γ-aminobuty-rate transaminase. The two could be distinguished by their dramatically different activities on β-alanine (100 vs. 3) and γ-aminobutyrate (43 vs.100), respectively, as well as their distinct amino acceptor requirements.

Burnett et al., *J. C. S. Chem. Comm.*, 1979, 826-828, suggested omega-amino acid:pyruvate transaminase and γ-aminobutyrate transaminase exhibit different preferences for the two terminal hydrogen atoms in tritium labelled γ-aminobutyrate.

Tanizawa et al., *Biochem.* 21, 1104-1108 (1982) examined bacterial L-lysine-ε-aminotransferase and L-ornithine-δ-aminotransferase and noted that while both are specific for L-amino acids, they act distally and with the same stereospecificity as the γ-aminobutyrate transaminase studied by Burnett et al., supra.

Yonaha et al., *Agric. Biol. Chem,*, 47 (10), 2257-2265 (1983) subsequently characterized omega-amino acid:-pyruvate transaminase and γ-aminobutyrate transaminase (EC 2.6.1.18 and EC 2.6.1.19) and documented their distribution in a variety of organisms.

Waters et al., *FEMS Micro. Lett.*, 34 (1986) 279-282, reporting on the complete catabolism of β-alanine and β-aminoisobutyrate by *P. aeruginosa*, noted that the first step involved transamination with β-alanine:pyruvate aminotransferase.

Enzymatic methods have been considered as a method for separating mixtures of chiral amines which are not amino acids, as for example 2-aminobutanol. Most of these involve derivatization, particularly of the amino group, and utilization of this protected group or another group in the molecule to effect separation. EP-A 222,561, for example, describes a process in which racemic 2-aminobutanol is converted to an N-carbamoyl derivative which then is brought into contact with an alkyl alkanoate in the presence of a lipase enzyme. Esterification of the free hydroxy group apparently is limited to the S-enantiomer of the N-carbamoyl derivative, which is thereafter hydrolysed. This process of course is necessarily limited to amines carrying an esterifiable hydroxy group and, moreover, specifically requires prior protection of the amino group through formation of —NH—CO— carbamoyl group in order to obtain stereospecificity in enzymatic reaction.

EP-A 239,122 describes a similar process applicable to the broader class of 2-amino-1-alknols.

Japanese Kokai JP 55-138,389 describes the preparation of vicinal amino alcohols by subjecting an alkyl or aralkyl substituted ethyleneimine to microorganisms of the genus Bacillus, Proteus, Erwinia, or Klebsiella.

Japanese Kokai JP 58-198,296 discloses a process in which d,l N-acyl-2-aminobutanol is subjected to the action of an aminoacylase derived from various species of Asperigillus, Penicillium, and Streptomyces which hydrolyses only the d-N-acyl-2-aminobutanol.

Japanese Kokai JP 59-39,294 describes a process for resolving racemic 2-aminobutanol through formation of an N-acetyl derivative which is treated with a Micrococcus acylase to give 1-2-aminobutanol and d-N-acetyl-2-aminobutanol, the latter then being chemically hydrolysed to afford d-2-aminobutanol.

Japanese Kokai JP 63-237796 describes a process in which R,S-1-methyl-3-phenylpropylamine is cultured aerobically in a variety of specified microorganisms with the S-form being metabolized preferentially. The highest yields and optical purity is reported for the yeast species *Candida humicola* and *Trichosporon melibiosaceum*. The enzymatic nature of the metabolism of the S-form which occurs in these aerobic cultures, e.g., an oxidase, dehydrogenase, ammonia lysase, etc., is not indicated.

The abstract of Japanese Kokai JP 63-273486 discloses the microbial synthesis of 1-(4-methoxyphenyl)-2-aminopropane with the R-configuration at one of the two chiral centers from 1-(4-methoxyphenyl)-2-propanone with *Sarcina lutea*.

DETAILED DESCRIPTION

In its broadest sense, the present invention involves the use of an omega-amino acid transaminase in the presence of an amino acceptor to enantiomerically enrich a mixture of, or to stereoselectively synthesize, chiral amines in which the amino group is bound to a non-terminal, chirally substituted, carbon atom. Thus the invention is based on the discovery that omega-amino acid transaminases operate stereoselectively on amino groups which are not in an omega position and that this action can be used both for enantiomeric enrichment of a mixture of chiral amines and stereoselective synthesis of a chiral amine of only one configuration.

By the term omega-amino acid transaminases is meant any enzymes which exhibits the property of converting the terminal $-CH_2-NH_2$ group of an omega-amino acid to a $-CH=O$ group.

The enzymatic equilibrium reaction involved in the present invention can be depicted as follows:

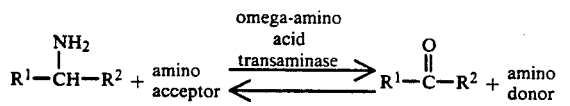

in which each of $R^1$ and $R^2$, when taken independently, is an alkyl or aryl group which is unsubstituted or substituted with one or more enzymatically non-inhibiting group and $R^1$ is different from $R^2$ in structure or chirality, or $R^1$ and $R^2$, taken together, are a hydrocarbon chain of 4 or more carbon atoms containing a center of chirality.

As used herein, "amino acceptor" refers to various carbonyl compounds, more fully discussed below, which are capable of accepting an amino group from the depicted amine under the influence of an omega-amino acid transaminase. "Amino donor" refers to various amino compounds, more fully discussed below, which are capable of donating an amino group to the depicted ketone, thereby becoming a carbonyl species, also under the influence of the same omega-amino acid transaminase.

The enzymatic reaction depicted above is characterized firstly by the fact that the omega-amino acid transaminase operates on a primary amine in which the amino group is not in an omega (or terminal) position. Secondly, the transaminase operates on an amine which need not be an amino acid. Thirdly, the consumed amine product of the enzymatic transformation is not irreversibly metabolized but can be stereoselectively reconverted to the starting amine of a uniform chirality.

In a first embodiment, the present invention provides a process for the enantiomeric enrichment of a mixture of chiral amines of the formula:

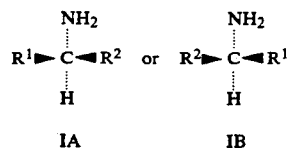

in which each of $R^1$ and $R^2$ are as defined above through the action of an omega-amino acid transaminase in the presence of an amino acceptor. As can be seen, the compounds of Formulas IA and IB are enantiomers (or diastereomers if either $R^1$ or $R^2$ contains a second chiral center) and are chiral by reason of $R^1$ being different in structure or chirality from $R^2$.

In a second embodiment, the invention provides a process for the stereoselective synthesis of one chiral form of an amine of formula IA or IB in an amount substantially greater than the other by subjecting a ketone of the formula:

in which $R^1$ and $R^2$ are as defined above to the action of an omega-amino acid transaminase in the presence of an amino donor.

Both embodiments are based on the discovery that the action of an omega-amino acid transaminase is not limited to omega-amino groups and moreover is largely or exclusively stereoselective with respect to amines of the defined class, converting only one chiral form of the amine to the corresponding ketone which is no longer chiral (at least with respect to the carbonyl carbon atom) and in turn converting that ketone to only one chiral form of the amine.

The term "enantiomeric enrichment" as used herein refers to the increase in the amount of one enantiomer as compared to the other. This can involve (i) a decrease in the amount of one chiral form as compared with the other, (ii) an increase in the amount of one chiral form as compared with the other, or (iii) a decrease in the amount of one chiral form and an increase in the amount of the other chiral form. A convenient method of expressing the enantiomeric enrichment achieved is the concept of enantiomer excess, or "ee", expressed by the expression:

$$ee = \frac{E^1 - E^2}{E^1 + E^2} \times 100$$

in which $E^1$ is the amount of the first chiral form of the amine and $E^2$ is the amount of the second chiral form of the same amine. Thus if the initial ratio of the two chiral forms is 50:50 and an enantiomeric enrichment sufficient to produce a final ratio of 50:30 is achieved, the ee with respect to the first chiral form is 25%, whereas if the final ratio is 70:30, the ee with respect to the first chiral form is 40%. Typically with the process of the present invention, ee's of 90% or greater can be achieved.

"Substantially greater" as used herein with reference to the stereoselective synthesis of one chiral form of an amine over the other refers to a ratio of at least about 3:1, representing an ee of at least about 50%.

The chiral amines of Formulas IA and IB employed in the present process have several structural restraints. First while the amino group is a primary amine, it must be bound to a secondary carbon atom; i.e., a carbon atom carrying one hydrogen atom and two substituents which are other than hydrogen ($R^1$ and $R^2$). Secondly, while $R^1$ and $R^2$ are selected from the same types of structure, these groups must render the molecule chiral; i.e., $R^1$ necessarily will be different from $R^2$ in structure or chirality or $R^1$ and $R^2$ when taken together are a chiral group. Generally when taken independently, $R^1$ and $R^2$ will be alkyl, aralkyl, or aryl groups, preferably a straight or branched alkyl group of from 1 to 6 carbon atoms, a straight or branched phenyl-alkyl group of from 7 to 12 carbon atoms, or a phenyl or naphthyl group. Examples include methyl, ethyl, n-propyl, i-propyl, n-butyl, i-butyl, s-butyl, phenyl, benzyl, phenethyl, 1-phenethyl, 2-phenylpropyl, etc. Moreover, since the enzymatic reaction of the present invention involves the depicted amino group and its associated carbon atom, each $R^1$ and $R^2$ group optionally can be substituted with one or more groups, provided the same are not enzymatically inhibiting groups, that is, groups which do not significantly affect or compete with the action of the transaminase when the chiral amine or ketone carrying that group are present in practical concentrations. This can be readily determined by a simple inhibition assay. Often when inhibition is detected, it can be minimized by conducting the reaction at lower concentrations of that reactant. Typical substituents without limitation include halo such as chloro, fluoro, bromo and iodo, hydroxy, lower alkyl, lower alkoxy, lower alkylthio, cycloalkyl, carbamoyl, mono- and di-(lower alkyl) substituted carbamoyl, trifluoromethyl, phenyl, nitro, amino, mono- and di-(lower alkyl) substituted amino, alkylsulfonyl, arylsulfonyl, alkylcarboxamido, arylcarboxamido, etc.

Typical groups when $R^1$ and $R^2$ are taken together are 2-methylbutane-1,4-diyl, pentane-1,4-diyl, hexane-1,4-diyl, hexane-1,5-diyl, and 2-methylpentane-1,5-diyl.

Typical amines for which the present process is suitable include without limitation 2-aminobutane, 2-amino-1butanol, 1-amino-1-phenylethane, 1-amino-1-(2-methoxy-5-fluorophenyl)ethane, 1-amino-1-phenylpropane, 1-amino-1-(4hydroxyphenyl)propane, 1-amino-1-(4-bromophenyl)propane, 1-amino-1-(4-nitrophenyl)-propane, 1-phenyl-2-aminopropane, 1-(3-trifluoromethylphenyl)-2-aminopropane, 2-aminopropanol, 1-amino-1-phenylbutane, 1-phenyl-2-aminobutane, 1-(2,5-di-methoxy-4-methylphenyl)-2-aminobutane, 1-phenyl-3-aminobutane, 1-(4-hydroxyphenyl)-3-aminobutane, 1-amino-2-methylcyclopentane, 1-amino-3-methylcyclopentane, 1-amino-2-methylcyclohexane, 1-amino-1-(2-naphthyl)ethane, 3-methylcyclopentylamine, 2-methylcyclopentylamine, 2-ethylcyclopentylamine, 2-methylcyclohexylamine, and 3-methylcyclohexylamine, 1-aminotetralin, 2-aminotetralin, 2-amino-5-methoxytetralin, and 1-aminoindan.

In its broadest sense, the process of the first embodiment comprises subjecting a mixture of chiral amines to the action of an omega-amino acid transaminase which is enzymatically active (with respect to the depicted amino group of at least one of said chiral amines) in the presence of an amino acceptor.

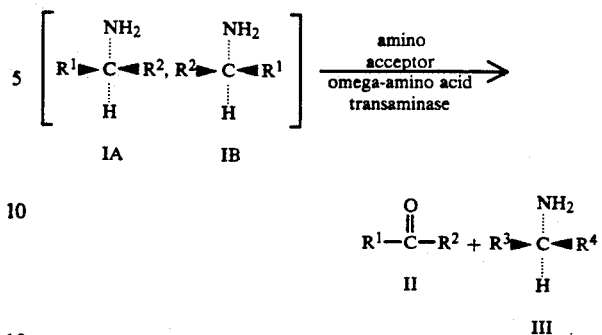

in which $R^1$ and $R^2$ are as defined above and, in Formula III, either $R^3$ is $R^1$ while $R^4$ is $R^2$ or $R^3$ is $R^2$ while $R^4$ is $R^1$.

In general, the enzymatic process operates on only one chiral form, or operates on one chiral form to a far greater extent than the other. For example, with R,S-1-amino-1-phenylethane ($R^1$= phenyl, $R^2$= methyl), only the S-form is converted to the respective nonchiral ketone, acetophenone, leaving the R-1-amino-1-phenylethane unchanged. Similarly with R,S-1-amino-1-(4-bromophenyl)ethane ($R^1$=4-bromophenyl, $R^2$= methyl), the S-form is converted to the nonchiral ketone 4-bromoacetophenone, while R-1-amino-1-(4-bromophenyl)ethane is unchanged. With R,S-1-phenyl-3-aminobutane ($R^1$= phenethyl, $R^2$= methyl), the S-form is readily converted to the nonchiral 1-phenylbutan-3-one whereas the R-form of 1-phenyl-3-aminobutane is converted to 1-phenylbutan-3-one by a factor of 0.05 or less than that of the S-form.

In some instances it is possible to assign $R^1$ and $R^2$ configurations to the chiral amines and identify which is converted to the ketone and which is not. Assignment of R- and S- designations are made, however, according to the Cahn-Ingold-Prelog method and depend upon preassigned values for $R^1$ and $R^2$ in the Sequence Rule. Consequently, a priori assignment of an R- or S- chirality designation to the chiral amine which is acted upon by the enzyme is not always possible. Hence while assignment of an R- or S- configuration to the chiral amine of Formula III will depend on the ranking of $R^3$ and $R^4$ according to the Sequence Rule, the configuration of the chiral amine of Formula III will be identical with one, but only one, of the enantiomers IA and IB. For example and as noted above, the S-form of 1-amino-1-phenylethane is converted to the nonchiral ketone, acetophenone, leaving the R-enantiomer unchanged. With R,S-1-amino-1-phenyl-2-hydroxyethane (phenylglycinol), the enantiomer having the same absolute configuration as that of 1-amino-1-phenylethane is converted but because of the Sequence Rule, this is designated the R-isomer.

Since the reaction is an equilibrium, either the forward or reverse reactions can be favored by the addition of additional starting materials or the removal of reaction products. When, for example, one desires to enrich the enantiomeric ratio of two chiral forms of an amine, additional quantities of the amino acceptor can be added (up to saturation) and/or the ketone formed can be continuously removed from the reaction mixture. Conversely when one stereoselectively synthesizes one chiral form of an amine, additional ketone can be added (up to saturation) and/or the amine formed can be removed.

When the undesired chiral form of the amine is converted to the ketone and the desired chiral form is not, the latter can be readily isolated by conventional techniques. Thus a partial separation can be effected by acidification, extraction with a hydrocarbon such as heptane to remove the ketone, rendering the aqueous phase basic, and re-extraction with a hydrocarbon such as heptane.

Often the by-products so isolated are themselves useful commodities. For example, if the process is practiced so as to enantiomerically enrich a mixture of R-2-aminobutane and S-2-aminobutane ($R^1$= ethyl, $R^2$= methyl) with the R-chiral form, the S-chiral form will be converted to methyl ethyl ketone, itself a useful organic solvent.

When, on the other hand, both chiral forms of the amine are desired, the form which is converted to the ketone can be removed from the reaction mixture (or from the aqueous phase in a two phase mixture) and independently subjected to the action of an omega-amino acid transaminase in the presence of a amino donor to generate the same chiral form as was initially converted to the ketone. For example, starting with a mixture of R,S-1-amino-1-phenylethane ($R^1$= phenyl, $R^2$= methyl), the S-form is converted by the omega-amino acid transaminase to the respective nonchiral ketone, acetophenone, leaving the R-1-amino-1-phenylethane unchanged. The R-1-amino-1-phenylethane is readily isolated from the reaction mixture as described above and the acetophenone by-product in turn is subjected to the action of the transaminase in the presence of an amino donor to generate S-1-amino-1-phenylethane in a substantially higher percentage than is the R-form.

The second aspect of the foregoing process can be practiced apart from the first. Hence the stereoselective synthesis of one chiral form of an amine of the formula:

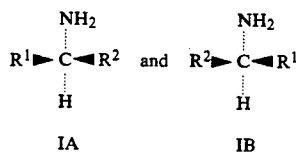

IA    IB in an amount substantially greater than the other can be achieved by subjecting a ketone of the formula:

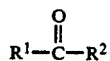

II in which $R^1$ and $R^2$ are as defined above to the action of an omega-amino acid transaminase in the presence of an amino donor until a substantial amount of one of the chiral amines is formed. In the example given above, for example acetophenone is subjected to the action of the transaminase in the presence of an amino donor to generate the S-1-amino-1-phenylethane exclusive of, or in a substantially higher percentage than, R-1-amino-1-phenylethane.

The amino acceptors are ketocarboxylic acids, alkanones, or substances converted thereto in situ. Typical of the ketocarboxylic acids are α-keto carboxylic acids such as glyoxalic acid, pyruvic acid, oxaloacetic acid, and the like, as well as salts thereof. A typical alkanone is butan-2-one.

In addition, one can employ other substances which are converted to an amino acceptor by other enzymes or whole cell processes. Representative of substances converted to these amino acceptors is fumaric acid (which is rapidly converted to oxaloacetic acid in situ), glucose, (which is converted to pyruvate), lactate, maleic acid, etc.

The amino donors are amines including the nonchiral amino acid glycine and chiral amino acids having the S-configuration such as L-alanine or L-aspartic acid. Amines, both chiral and non-chiral, which are not amino acids such as S-2-aminobutane, propyl amine, benzyl amine, etc. also can be employed.

Omega-amino acid transaminases useful in the present process are known pyridoxal phosphate dependent enzymes found in various microorganisms including Pseudomonas, Escherichia, Bacillus, Saccharomyces, Hansenula, Candida, Streptomyces, Aspergillus, and Neurospora. Two omega-amino acid transaminases which are particularly useful in the present invention, EC 2.6.1.18 and EC 2.6.1.19, have been crystallized and characterized by Yonaha et al., *Agric. Biol. Chem.*, 47 (10), 2257–2265 (1983).

Microorganisms having the desired activity can be readily isolated by chemostat culture, that is, culturing in a constant but restricted chemical environment, with an amino acceptor and, as the sole nitrogen source, an amine. The amine can be, but need not be, a chiral amine since in a normal environment omega-amino acid transaminases metabolize primary amines. Non-chiral amines which have been used successfully to generate omega-amino acid transaminase include n-octylamine, cyclohexylamine, 1,4-butanediamine, 1,6-hexanediamine, 6-aminohexanoic acid, 4-aminobutyric acid, tyramine, and benzyl amine. Chiral amines such as 2-amino -butane, α-phenethylamine, and 2-amino-4-phenylbutane also have been used successfully, as have amino acids such as L-lysine, L-ornithine, β-alanine, and taurine.

By such a procedures the culture will be enriched for those microorganisms producing the desired omega-amino acid transaminases. For example, in one such chemostat conducted with random soil samples having no particular history of amine exposure was run for approximately one month. The dominant organisms thereafter were independently identified by the American Type Culture Collection as *Bacillus megaterium* which did not differentiate significantly from and were phenotypically similar to known strains.

Organisms so isolated can be grown in a number of ways. Firstly, a standard salts medium supplemented with phosphate buffer, sodium acetate as a carbon source, 2-ketoglutarate as an amino acceptor, and a nitrogen-containing compound such as n-propylamine, n-octylamine, 2-aminobutane, 2-aminoheptane, cyclohexylamine, 1,6-hexanediamine, putrescine, 6-aminohexanoic acid, 4-aminobutyric acid, L-lysine, L-ornithine, β-alanine, α-phenethylamine, 1-phenyl-3-aminobutane, benzylamine, tyramine, taurine, etc. can be used.

Alternatively the microorganism can be grown using an amine as the sole carbon source, thereby limiting growth to those organisms which can catabolize the amine to obtain carbon.

Thirdly, the microorganism can be grown using sodium succinate, sodium acetate, or any other carbon source and an ammonium salt or a protein hydrolysate as the principle nitrogen source and then adding, either at the outset or during growth, an amine such as 2-aminobutane, 1-phenyl-3-aminobutane, α-phenethylamine, etc., to induce production of the desired transaminase activity.

The actual enzymatic conversion can be effected by conventional culturing techniques in the presence of the chiral amine, with isolated but non-growing cells, or by bringing the chiral amines into contact with a soluble omega-amino acid transaminase preparation.

The omega-amino acid transaminase can be in free form, either as a cell free extract or a whole cell preparation as noted above, or immobilized on a suitable support or matrix such as cross-linked dextran or agarose, silica, polyamide, or cellulose. It also can be encapsulated in polyacrylamide, alginates, fibers, or the like. Methods for such immobilization are described in the literature (see, for example, *Methods of Enzymology*, 44, 1976). The latter embodiment is particularly useful since once the immobilized enzyme is prepared, one need merely feed the amino acceptor and a mixture of the chiral amines over the immobilized enzyme in order to effect the desired enrichment, and then remove the formed ketone in the manner described above.

Although not necessary, it generally is advantageous to maximize conversion rates if a source of pyridoxamine, such as pyridoxal phosphate, is included in the reaction composition.

Procedures and materials used herein are described below, followed by typical examples.

Procedures and Materials

Enzyme Activity:

Enzyme activity is expressed herein as units/mg. A unit of enzyme activity is defined as that which produces 1 micromole of ketone per minute. For uniformity, this is measured as micromoles of 1-phenylbutan-3-one formed from R,S-1-phenyl-3-aminobutane. The following standardized assay was utilized to measure the activity of the omega-amino acid transaminases set forth in the examples which follow.

A known volume of the enzyme preparation to be tested is incubated at 37° C. and pH 7 in a solution having the following composition:

| Sodium pyruvate | 100 mM |
| R,S-1-Phenyl-3-aminobutane | 30 mM |
| Pyridoxal phosphate | 0.5 mM |

A sample is removed and 20% by volume of 12% aqueous trichloroacetic acid are added. Precipitated protein is removed by centrifugation and the concentration of 1-phenyl-butan-3-one in the supernatant is determined by liquid chromatography on a 100×8 mm 4 micron Novopak phenyl column eluting with 40% isopropanol and 0.09% phosphoric acid in water. Under these conditions, 1-phenylbutan-3-one elutes at 5.3 minutes.

Purity of Amines:

The purity of produced amines was determined by gas chromatograpy on a 6 foot ×2 mm Chrom Q column of 10% SE-30 on a 100/120 mesh support at 210° C. with a carrier gas flow rate of 10 mL/minute.

Determination of Enantiomeric Enrichment:

The ee of a given product was determined by reaction with (−) α-(tri-fluoromethylphenyl)methoxyacetyl chloride (see Gal, *J. Pharm. Sci.*, 66, 169 (1977) and Mosher et al., *J. Org. Chem.*, 34, 25430 (1969)) followed by capillary gas chromatography of the derivatized product on a Chrompack fused silica column.

Standard Salt Medium:

A suitable salt medium for the microbiological transformations described in the following examples has the following composition:

| $MgSO_4$ | 1.00 g/L |
| $CaCl_2$ | 0.021 g/L |
| $ZnSO_4.7H_2O$ | 0.20 mg/L |
| $MnSO_4.4H_2O$ | 0.10 mg/L |
| $H_3BO_3$ | 0.02 mg/L |
| $CuSO_4.5H_2O$ | 0.10 mg/L |
| $CoCl_2.6H_2O$ | 0.05 mg/L |
| $NiCl_2.6H_2O$ | 0.01 mg/L |
| $FeSO_4$ | 1.50 mg/L |
| $NaMoO_4$ | 2.00 mg/L |
| Fe EDTA | 5.00 mg/L |
| $KH_2PO_4$ | 20.00 mM |
| NaOH | to pH 7 |

The composition is not critical but was standardized for all procedures to eliminate it as a variable.

Microorganisms:

Cultures either were obtained from the designated depository or were isolated as described and then independently identified.

Enrichment of Microorganisms Producing omega-Amino Acid Transaminase:

A chemostat is maintained with 0.5% (w/v) of R,S-2-aminobutane and 10 mM of 2-ketoglutarate at a dilution rate of 0.03 h in the standard salt medium. The chemostat is inoculated and run for approximately one month at 37° C. and pH 6.8–7.0. Strains which develop are isolated and grown on minimal agar containing the standard salt medium supplemented with 10 mM of 2-ketoglutarate and 5 mM of R,S -1-phenyl-3-aminobutane.

Enzyme Recovery:

Unless otherwise indicated, cells from culture are centrifuged for 10 minutes at 10,000 G, resuspended in 10 mM of phosphate buffer at pH 7 and 0.5 mM of pyridoxal phosphate, and ruptured by two passes through a chilled French press operating at 15,000 psi. Cell debris is removed by centrifugation for one hour at 10,000 G and the enzyme-containing supernatant collected.

The following examples will serve to further typify the nature of this invention but should not be construed as a limitation on the scope thereof, which is defined solely by the appended claims.

EXAMPLE 1

The following procedure exemplifies the growth of microorganisms producing omega-amino acid transaminase using an amino donor as the sole source of nitrogen.

*Bacillus megaterium* was grown in a 3L shake flask (200 rpm) for 17 hours at 30° C. with 1L of the above salt solution, 60 mM of sodium acetate, 30 mM of phosphate buffer, 30 mM of disodium 2-ketoglutarate, and 100 mm of n-propylamine as the nitrogen source. When the culture reached a density of 0.6 g (dry weight)/L, the cells were harvested and the enzyme isolated as described above. The specific activity of the omega-amino acid transaminase thus obtained when assayed as above was 0.49 units/mg.

The *Bacillus megaterium* strain used in the foregoing procedure was obtained from soil samples with no particular history of exposure to amines by inoculating the chemostat previously described and isolating the dominant organisms (those capable of growing on R,S-1-phenyl-3-aminobutane). The strain was independently identified by the American Type Culture Collection as *Bacillus megaterium* which did not differentiate significantly from the known strain ATCC No. 14581 and which was phenotypically similar to ATCC 49097B.

EXAMPLE 2

The following procedure exemplifies the growth of microorganisms producing omega-amino acid transaminase using the amino donor as the sole source of carbon.

*Pseudomonas aeruginosa* ATCC 15692 was grown on β-alanine as the sole carbon source as described by Way et al., *FEMS Micro. Lett.*, 34, 279 (1986) and cell extracts containing the omega-amino acid transaminase then are obtained as therein described. When assayed as described above, the specific activity of the omega-amino acid transaminase was found to be 0.040 units/mg.

EXAMPLE 3

*Pseudomonas putida* ATCC 39213 was cultured as described in Example 1 and an enzyme extract then was obtained as therein described. The specific activity of the omega-amino acid transaminase was 0.045 units/mg.

EXAMPLE 4

The following procedure demonstrates the need for the amino acceptor.

Enzyme extracts from *P. putida*, *B. megaterium*, and *P. aeruginosa* obtained as above were assayed as above at pH 9 in 50 mM of Tris/HCl using 30 mM of R,S-1-phenyl-3-aminobutane, with and without 100 mM of sodium pyruvate. The following relative rates of conversion were observed.

|  | Relative Rate of Conversion | | |
| --- | --- | --- | --- |
|  | P. putida | B. megaterium | P. aeruginosa |
| pyruvate | 100 | 100 | 100 |
| no pyruvate | 0 | 0 | 0 |

The transaminase nature of the enzymatic action is apparent from the effect of "suicide inactivators" known to be specific for transaminases {see, for example, Burnett et al., *J. Bio. Chem.*, 225, 428–432 (1980)}, the inactivator (0.5 mM) being preincubated with the assay medium before addition of R,S-1-phenyl-3-aminobutane.

| | Relative Rate of Conversion | | |
| --- | --- | --- | --- |
| Inactivator | P. putida | B. megaterium | P. aeruginosa |
| None | 100 | 100 | 100 |
| Gabaculine | 0 | 13 | 0 |
| Hydroxylamine | 3 | 10 | 0 |

The stereoselectivity of the omega-amino acid transaminase can be seen from the corresponding assay utilizing 15 mM of R-1-phenyl-3-aminobutane (with pyruvate).

| | Relative Rate of Conversion | | |
| --- | --- | --- | --- |
| | P. putida | B. megaterium | P. aeruginosa |
| R,S- | 100 | 100 | 100 |
| R- | 3 | 15 | 4 |

EXAMPLE 5

The following procedure exemplifies the growth of microorganisms using ammonium as the sole nitrogen source and then inducing omega-amino acid transaminase production by the addition of an amine.

*Bacillus megaterium* was grown in 1L cultures in the standard salt medium supplemented with 40 mM of the indicated carbon source, 5 mM of ammonium chloride, 80 mM of phosphate buffer, and 2 mM of the amine inducer indicated below. After 30 to 40 hours, the enzyme was collected and assayed as described above.

| | Specific Activity (units/mg) | | | |
| --- | --- | --- | --- | --- |
| Carbon Source | Succinate | Acetate | Gluconate | Glucose |
| R,S-1-phenyl-1-aminoethane | 0.27 | 0.39 | n.t. | n.t. |
| R-1-phenyl-1-aminoethane | 0.27 | 0.36 | n.t. | n.t. |
| R,S-1-phenyl-3-aminobutane | 0.28 | 0.33 | 0.26 | 0.62 |
| R-1-phenyl-3-aminobutane | 0.21 | 0.26 | n.t. | n.t. |
| R,S-2-aminobutane | 0.13 | 0.14 | n.t. | n.t. |
| R-2-aminobutane | 0.06 | 0.13 | n.t. | n.t. |
| tyramine | n.t. | 0.24 | n.t. | n.t. | n.t. = not tested

EXAMPLE 6

The following procedure exemplifies the growth of microorganisms using a protein rich source and then inducing omega-amino acid transaminase production by the addition of an amine.

*Bacillus megaterium* was grown in 121L fermenter at pH 7° and 30° C. with aeration and agitation in the above salt medium supplemented with 10 g/L casamino acids. Sodium acetate was added gradually up to an aggregate concentration of 120 mM. At this point, the cell density was 3 g (dry weight)/L. 1-Phenyl-3-aminobutane was added up to an aggregate concentration of 10 mM. After 12 hours, the enzyme was collected and assayed as described above. The specific activity was 0.49 units/mg.

EXAMPLE 7

The following procedure exemplifies the use of a soluble enzyme preparation to effect enantiomeric enrichment of a racemate of a chiral amine.

An omega-amino acid transaminase preparation was obtained from *Bacillus megaterium* in the manner described in Example 1. Upon assay as described above, it demonstrated a specific activity of 0.375 units/mg. To a 25 mL solution of 26.4 mg of this enzyme preparation, additionally containing 0.4 mM of pyridoxal phosphate and 40 mM of sodium phosphate, were added 20 mM of R,S-1-amino-1-phenylethane and 100 mM of sodium pyruvate as the amino acceptor. The solution was incubated for 150 minutes at pH 7° and 30° C. and then rendered alkaline (pH >12) by the addition of 2.5 mL of 2N sodium hydroxide. The solution was extracted with n-heptane and the extracts evaporated to yield 30.8 mg (49% conversion) of R-1-amino-1-phenylethane having an ee of 96.4%.

EXAMPLE 8

The following procedures exemplify the use of a soluble enzyme preparation to effect enantiomeric enrichment of a racemate of a chiral amine.

By substituting a corresponding amount of R,S-1-phenyl-3-aminobutane for R,S-1-amino-1-phenylethane in the procedure of Example 7, R-1-phenyl-3-aminobutane is obtained in 60% conversion with an ee of 98.4%.

By substituting a corresponding amount of R,S-1-amino-1-(4-bromophenyl)ethane for R,S-1-amino-1-phenylethane in the procedure of Example 7, R-1-amino-1-(4-bromophenyl)-ethane is obtained in 49% conversion with an ee of 97.6%.

EXAMPLE 9

The following procedure exemplifies the use of non-growing cells to effect enantiomeric enrichment of a racemate of a chiral amine.

The cells from three 1L cultures of *Bacillus megaterium* grown for 33 hours in the manner described in Example 1 on 6 mM of R,S-1-phenyl-3-aminobutane as the sole nitrogen source were harvested by centrifugation and washed by resuspension in 250 mL of 10 mM phosphate buffer (pH 6.8) and centrifugation.

The cell pellet was resuspended in 0.6L of 10 mM phosphate buffer (pH 6.8) containing 10 mM of R,S-1-phenyl-3-aminobutane and 50 mM of oxaloacetic acid as the amino acceptor. After incubation on an orbital incubator at 30° C. for 4 hours, the solution was rendered alkaline and extracted with heptane as described in Example 7. R-1-Phenyl-3-aminobutane thus was obtained in 97.9% optical purity, corresponding to an ee of 95.8.

EXAMPLE 10

The following procedure exemplifies the use of growing cells to effect enantiomeric enrichment of a racemate of a chiral amine and the use of an amino acceptor precursor.

A 6L innoculum of Bacillus megaterium, prepared substantially as described in Example 1 but using 10 mM of R,S -1-phenyl-3-aminobutane as the sole nitrogen source, was cultured in a 120L volume of the above salt medium supplemented with 30 mM of fumarate as the amino acceptor precursor. Twenty-two hours after inoculation, an additional 30 mM of fumarate was added and 6 hours later the culture was harvested by removing the cells through ultrafiltration using a Romicon PM100 membrane. The solution was rendered alkaline and extracted with heptane as described in Example 7. R-1-Phenyl-3-aminobutane thus was obtained in 99.5% purity with an ee of 96.4%.

Example 11

The following procedure exemplifies the relative rates of conversion, determined directly or calculated from kinetic data, of different chiral amines by soluble enzymatic preparations utilizing the assay described above but substituting the indicated chiral amine.

| Amine (R,S) | Conc. (mM) | Relative Rate of Conversion | |
|---|---|---|---|
| | | R-enantiomer | S-enantiomer |
| 1-phenyl-1-aminoethane | 10 | 0 | 100 |
| 1-phenyl-3-aminobutane | 30 | 5 | 100 |
| 1-(4-bromophenyl)-1-aminoethane | 30 | 0 | 100 |
| 1-(α-naphthyl)-1-aminoethane | 10 | 0 | 100 |
| phenylglycinol | 10 | 100 | 0 |
| 2-aminooctane | 5 | 0 | 100 |

EXAMPLE 12

The following procedure exemplifies the relative rates of conversation with 1-phenyl-3-aminobutane employing different amino acceptors in place of pyruvate in the assay described above.

| Acceptor | Conc. (mM) | Relative Rate of Conversion |
|---|---|---|
| pyruvate | 20 | 100 |
| oxaloacetate | 20 | 100 |
| heptaldehyde | 25 | 80 |
| glyoxalate | 20 | 50 |
| 2-ketobutyrate | 25 | 21 |
| butan-2-one | 20 | 20 |

Also found to be effective as amino acceptors although considerably less so (relative rates = <21) are 3-hydroxy-pyruvate, 2-pentanone, cyclopentanone, and acetophenone.

EXAMPLE 13

The following procedure exemplifies enantiomeric enrichment using a soluble enzyme preparation with continuous extraction of the enriched product.

A soluble enzyme preparation was obtained from *Bacillus megatarium* in the manner described in Example 1. Upon assay as described above, it demonstrated a specific activity of 0.70 units/mg. An aqueous phase was prepared containing 450 mg of this extract, 0.12M sodium pyruvate, 0.2M R,S-1-phenyl-3-aminobutane, 1 mM pyridoxal phosphate, and 0.5M phosphate (pH 7.5). Five hundred milliliters of n-heptane were added and the two phase mixture was stirred at 22° C. for seven hours. The pH was then adjusted to 4.5 by the addition of hydrochloric acid and the aqueous layer was separated from the organic layer. The aqueous layer was rendered alkaline by the addition of sodium hydroxide and extracted with heptane. Upon removal of the heptane, the residue was analyzed as containing 96% R-1-phenyl-3-aminobutane.

EXAMPLE 14

The following procedure typifies the synthesis of a chiral amine.

A soluble enzyme preparation was obtained from *Bacillus megatarium* in the manner described in Example 1. Upon assay as described above, it demonstrated a specific activity of 0.58 units/mg. To a 200 mL aqueous solution of 350 mg of this preparation, 0.4 mM of pyridoxal phosphate, and 40 mM of sodium phosphate, are added 4.2 mM of 1-phenylbutan-3-one and 100 mL of 2-aminobutane as the amine donor. The mixture was incubated at pH 7° and 30° C. for 4 hours, at which point R-1-phenyl-3-aminobutane was present in the reaction mixture at a concentration of 3.35 mM, corresponding to 80% conversion. The product was isolated by the addition of 40 mL of 10N sodium hydroxide and extraction of the alkaline aqueous solution with 250 mL of n-heptane. Upon evaporation of the heptane extracts, there were obtained 100.5 g of product which was analyzed by derivation as previously described and found to contain 96.4% of S-1-phenyl-3-aminobutane.

EXAMPLE 15

This procedure exemplifies the enzymatic separation and isolation of each of the R- and S-enantiomers.

The procedure for obtaining the R-enantiomer of R,S-1-amino-1-phenylethane described in Example 7 is followed through the incubation. Prior to rendering the incubation solution alkaline, however, it is extracted with n-heptane and the extracts are retained. The aqueous phase then is processed according to Example 7 to isolate R-1-amino -1-phenylethane as described therein.

Acetophenone is recovered from the retained heptane extracts by evaporation. By following substantially the same procedure as set forth in Example 14 but employing 2.3 mM of acetophenone in place of 1-phenylbutan-3-one, 56 mg of S-1-amino-1-phenylethane (100%) were obtained.

EXAMPLE 16

This procedure exemplifies the use of immobilized enzyme.

Immobilization:

A 47 mm diameter ACTIDISK (FMC Corp.) support matrix (0.4 g) was loaded into a housing (Millipore Sweenex) fitted with inlet and outlet tubing, a peristaltic pump, and reservoir. The matrix was washed sequentially, at ambient temperatures and a rate of 3 mL/min., with (1) 200 mL of 50 mM of phosphate buffer (pH 7) containing 0.5 mM pyridoxal phosphate over a period of 20 min., (2) 11 mL of a 4.6 mg/mL solution of enzyme obtained in the manner of Example 1 for 120 min., (3) 150 mL of 0.3M sodium chloride in 50 mM of phosphate buffer (pH 7) containing 0.5 mM pyridoxal phosphate for 30 minutes, and (4) 200 mL of 50 mM of phosphate buffer (pH 7) containing 0.5 mM pyridoxal phosphate over a period of 20 min.

Enrichment:

A 140 mL. solution of 10 mM R,S-1-phenyl-3-aminobutane, 100M of sodium pyruvate, 0.1 mM of pyridoxal phosphate, and 25 mM of potassium phosphate (pH 7) was circulated through the above matrix at ambient temperatures and a rate of 5 mL/min. After two hours, the circulating liquid was removed from the apparatus. The concentration of 1-phenylbutan-3-one formed was 5.2 mM while that of R-1-phenyl-3-aminobutane was 4.8 mM. The pH was adjusted to 12.5 and R-1-phenyl-3-aminobutane was isolated quantitatively by extraction with heptane. After removal of the heptane by evaporation, the product was analyzed as 92.8% R -1-phenyl-3-aminobutane.

EXAMPLE 17

Each of the following racemates was substituted for R,S-1-amino-1-phenylethane in the procedure of Example 7.
(a) R,S-1-phenoxy-2-aminopropane
(b) R,S-1-amino-1-(2-methoxyphenyl)ethane
(c) R,S-1-amino-1-(3-methoxyphenyl)ethane
(d) R,S-1-amino-1-(4-methoxyphenyl)ethane
(e) R,S-1-(4-methoxyphenyl)-3-aminobutane
(f) R,S-1-amino-1,2-diphenylethane
(g) R,S-1-amino-1,2,3,4-tetrahydronaphthalene
(h) R,S-2-amino-1,2,3,4-tetrahydronaphthalene
(i) R,S-2-amino-5-methoxy-1,2,3,4-tetrahydronaphthalene
(j) R,S-1-amino-1-(4-chlorophenyl)ethane
(k) R,S-1-amino-1-(4-methylphenyl)ethane
(l) R,S-1-aminoindane The following R-enantiomers, respectively, with the recited % conversion, were observed as the products:

| Product | ee | % Conversion |
| --- | --- | --- |
| (a) R-1-phenoxy-2-aminopropane | 98 | 50 |
| (b) R-1-amino-1-(2-methoxyphenyl)ethane | 99 | 49 |
| (c) R-1-amino-1-(3-methoxyphenyl)ethane | 99 | 49 |
| (d) R-1-amino-1-(4-methoxyphenyl)ethane | 99 | 49 |
| (e) R-1-(4-methoxyphenyl)-3-aminobutane | 96 | 58 |
| (f) R-1-amino-1,2-diphenylethane | 98.1 | 49 |
| (g) R-1-amino-1,2,3,4-tetrahydronaphthalene | 99 | 50 |
| (h) R-2-amino-1,2,3,4-tetrahydronaphthalene | 97 | 58 |
| (i) R-2-amino-5-methoxy-1,2,3,4-tetrahydronaphthalene | 99.5 | 50 |
| (j) R-1-amino-1-(4-chlorophenyl)ethane | 99 | 49 |
| (k) R-1-amino-1-(4-methylphenyl)ethane | 99 | 49 |
| (l) R-1-aminoindane | 99 | 50 |

EXAMPLE 18

Following the procedure of Example 7 but reducing the amount of R,S-1-amino-1-phenylethane to 5 mM, 20 mM of each of the indicated amino group acceptors was used in place of sodium pyruvate. The ee and % conversion for R-1-amino-1-phenylethane in each case are as follows:

| Amino Group Acceptors | ee | % Conversion to R-1-amino-1-phenyl-ethane |
| --- | --- | --- |
| (a) glyoxylic acid | 99 | 49 |
| (b) disodium oxalacetate | 99 | 49 |
| (c) methyl ethyl ketone | 96 | 48.5 |
| (d) pentan-2-one | 95 | 48 |
| (e) cyclohexanone | 96 | 48.5 |
| (f) cyclopentanone | 93 | 47 |
| (g) heptaldehyde | 99 | 49 |
| (h) butyraldehyde | 99 | 49 |
| (i) cyclohexane carboxaldehyde | 99 | 49 |

EXAMPLE 19

The procedure of Example 14 was followed using, however, 20 mM of acetophenone as the ketone and 100 mM of glycine as the amine donor compound. Twenty four hours after inoculation, the culture was centrifuged and the clear filtrate washed with heptane, rendered alkaline, and extracted with heptane. Upon removal of the solvent, 135 mg of S-1-amino-1-phenylethane (100%) was obtained.

Utilizing a like amount of L-aspartic acid in place of glycine, 173.5 mg of S-1-amino-1-phenylethane (100%) was obtained.

Similarly with 100 mM of L-alanine there was obtained 185 mg of 1-amino-1-phenylethane (100%).

What is claimed is:

1. A process for the enantiomeric enrichment of a mixture of two enantiomeric chiral amines of the formula:

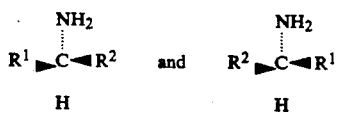

in which $R^1$ and $R^2$ together are a tetramethylene or pentamethylene chain, at least one hydrogen atom of which is replaced by an enzymatically non-inhibiting group which imparts chirality to said amine, which comprises bringing said mixture of chiral amines, in an aqueous medium and in the presence of an amino acceptor, into contact with an omega-amino acid transaminase which is enzymatically active with respect to the depicted amino group of one of said chiral amines, at least until a substantial amount of one of said chiral amines is converted to a ketone of the formula:

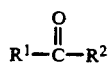

in which $R^1$ and $R^2$ are as defined for said amine.

2. The process of claim 1 in which said contact is maintained at least until the enantiomeric excess of the chiral amine which is not converted to said ketone is at least about 90% relative to the other chiral amine.

3. The process according to claim 1 wherein the chiral amine which is not converted to said ketone is recovered from the reaction mixture.

4. The process according to claim 1 wherein a substantial quantity of said ketone is recovered from the aqueous media.

5. The process according to claim 4 wherein the ketone recovered from the aqueous media is independently brought into contact with an omega-amino acid transaminase in the presence of an amine donor at least until the same chiral form as was initially converted to said ketone is formed in an amount substantially greater than the other chiral form is formed.

6. The process according to claim 1 wherein the amino acceptor is an α-keto carboxylic acid, an aliphatic or cycloaliphatic ketone, an aliphatic or cycloaliphatic aldehyde, or a substance which is biochemically converted to an α-keto carboxylic acid in situ in the reaction medium.

7. The process according to claim 6 wherein the amino acceptor is glyoxalic acid, pyruvic acid, oxaloacetic acid, a salt thereof, or heptaldehyde.

8. The process according to claim 1 wherein said mixture of chiral amines and amino acceptor are brought into contact with whole cells of a microorganism which produces omega-amino acid transaminase.

9. The process according to claim 1 wherein said mixture of chiral amines and amino acceptor are brought into contact with a cell-free aqueous preparation of said omega-amino acid transaminase.

10. The process according to claim 1 wherein said mixture of chiral amines and amino acceptor are brought into contact with said omega-amino acid transaminase immobilized on a support.

11. A process for the stereoselective synthesis of one chiral form of an amine of the formula:

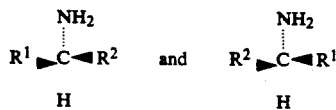

in an amount substantially greater than the other, in which $R^1$ and $R^2$ together are a tetramethylene or pentamethylene chain, at least one hydrogen atom of which is replaced by an enzymatically non-inhibiting group which imparts chirality to said amine, which comprises bringing a ketone of the formula:

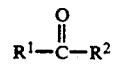

in which $R^1$ and $R^2$ are as defined for said amine into contact with an omega-amino acid transaminase in the presence of an amino donor at least until a substantial amount of one of said chiral amines is formed.

12. The process of claim 11 in which the amino donor is 2-aminobutane, glycine, alanine, or aspartic acid.

13. The process according to claim 11 wherein said ketone and amino donor are brought into contact with whole cells of a microorganism which produces omega-amino acid transaminase.

14. The process according to claim 11 wherein said ketone and amino donor are brought into contact with a cell-free aqueous preparation of said omega-amino acid transaminase.

15. The process according to claim 11 wherein said ketone and amino donor are brought into contact with said omega-amino acid transaminase immobilized on a support.

16. The process according to claim 11 wherein a large molar excess of said amino donor is employed.

* * * * *